United States Patent [19]
Bates et al.

[11] Patent Number: 5,691,812
[45] Date of Patent: Nov. 25, 1997

[54] CALIBRATION STANDARD FOR CALIBRATING A DEFECT INSPECTION SYSTEM AND A METHOD OF FORMING SAME

[75] Inventors: Eugene C. Bates, Ft. Mill, S.C.; Michael B. Ferrara, Charlotte, N.C.

[73] Assignee: ADE Optical Systems Corporation, Charlotte, N.C.

[21] Appl. No.: 620,890

[22] Filed: Mar. 22, 1996

[51] Int. Cl.$^6$ ........................................... G01J 1/02
[52] U.S. Cl. ............................................. 356/243
[58] Field of Search ........................ 356/243, 237, 356/336

[56] References Cited

U.S. PATENT DOCUMENTS

| | | | |
|---|---|---|---|
| 4,386,850 | 6/1983 | Leahy | 356/243 |
| 4,512,659 | 4/1985 | Galbraith et al. | 356/243 |
| 4,636,073 | 1/1987 | Williams | 356/243 |
| 5,004,340 | 4/1991 | Tullis et al. | 356/243 |
| 5,078,492 | 1/1992 | Scheer | 356/243 |
| 5,144,524 | 9/1992 | Tullis et al. | 263/293 |
| 5,198,869 | 3/1993 | Monteverde et al. | 356/243 |
| 5,214,486 | 5/1993 | DeWitt | 356/243 |
| 5,383,018 | 1/1995 | Sadjadi | 356/243 |

*Primary Examiner*—Frank G. Font
*Assistant Examiner*—Zandra V. Smith
*Attorney, Agent, or Firm*—Bell, Seltzer, Park & Gibson

[57] ABSTRACT

The calibration standard has artificial defects of a predetermined uniform size disposed on selected areas of a substrate. The artificial defects are randomly spaced within the selected area and of a sufficient density as to be visually discernable through a CRT display or other output device. The selected areas in which the artificial defects are disposed are formed by positioning a mask above the substrate. The open areas of the mask correspond to the selected areas on which the artificial defects are disposed. The form of these open areas may correspond to a character representing the predetermined size of the artificial defect. If this is the case, the operator can determine the size of the artificial defects on a substrate without reference to any external source. The method of calibrating the defect inspection system includes positioning the calibration standard within the defect inspection system, measuring the size of the artificial defects detected by the inspection system, identifying the size of the artificial defects by viewing the indicia on the substrate, and comparing the size indicated by the indicia to the size actually measured by the defect inspection system.

20 Claims, 3 Drawing Sheets

CALIBRATION STANDARD FOR CALIBRATING A DEFECT INSPECTION SYSTEM AND A METHOD OF FORMING SAME

FIELD OF INVENTION

The invention relates to calibration standards and methods of forming calibration standards for defect inspection systems.

BACKGROUND OF THE INVENTION

The presence of sub-micron sized particles and other microscopic defects or contaminants is detrimental to the quality of manufactured semiconductor devices. Semiconductor device manufacturers have made extensive use of defect inspection systems to detect defects on the silicon wafers used in the manufacture of semiconductor devices. Typically, these defect inspection systems are used at multiple points in the manufacturing process. Defect inspection systems of this general type are disclosed, for example, in U.S. Pat. No. 5,448,364 by Moran titled "Particle Detection System With Reflective Line-To-Spot Collector"; U.S. Pat. No. 5,329,351 by Clementi titled "Particle Detection System With Coincident Detection"; U.S. Pat. No. 5,127,726 by Moran titled "Method And Apparatus For Low Angle, High Resolution Surface Inspection"; U.S. Pat. No. 4,630,276 by Moran titled "Compact Laser Scanning System"; and U.S. Pat. No. 4,376,583 by Alford et al. titled "Surface Inspection Scanning System."

The accuracy of the defect inspection system depends on the ability of the operator to quickly and accurately calibrate the systems on a routine basis. In order to properly calibrate the defect inspection systems, artificial defects of a known size are introduced on calibration wafers. In prior calibration methods, these defects have generally taken the form of pits etched into the surface of the wafer, islands or pads formed on the surface of the wafer, or polystyrene latex spheres deposited on the wafer surface. The operator selects a calibration wafer with defects of the appropriate size, then calibrates the inspection system to the size of the selected defect.

A problem, however, arises in that the operator has trouble determining the size of the artificial defects selected without reference to data external to the wafer. For example, a group of calibration wafers may be stored in a storage device in which each slot in the storage device is labelled for a particular size defect, or the wafer may be stored in some protective covering on which the size of the artificial defects present on that wafer are displayed. If the wafer is not immediately returned to the storage device or the protective covering, however, a different wafer with different sized artificial defects may be placed in the incorrect slot in the storage device or in the protective covering by mistake.

Because there are no methods to verify the size of the artificial defects by examining the wafer, the operator has trouble determining which wafer contains the artificial defects corresponding to the external data located on the storage slot or protective covering. Even if the wafer is immediately returned to the storage device or protective covering, the step requiring the operator to cross-reference the defect size against some external data source takes additional time and provides an opportunity for additional mistakes.

The manufacturer can eliminate mistakes and reduce calibration times if the operator can determine the size of the artificial defects on a calibration wafer by visual inspection of the wafer, without reference to any source external to the wafer. For example, U.S. Pat. No. 4,386,850 by Leahy titled "Calibration Device And Method For An Optical Defect Scanner" describes a calibration device in which artificial defects are evenly spaced in multiple grids, where each grid is comprised of artificial defects of uniform sized within the grid, but of a different size from the artificial defects of other grids, and where some of the defects in the grid may be omitted to form numbers depicting the size of the defects in a particular grid. Because Leahy's patent requires the defects be evenly spaced in a grid format, however, the complexity of the pattern is limited and the specific point at which areas representing numbers indicated by the omission of artificial defects and areas where the artificial defects are present is unclear. Simple patterns of a few straight lines can be formed using the invention illustrated in Leahy's patent. Complex patterns, however, which include curves or multiple digits are less likely to be clearly discernable.

Clarity is further obscured by the small size of the grids illustrated in the Leahy patent. The largest grid shows 169 dots, thirteen dots along each side in the shape of a square. With the longest distance between one artificial defect and another of 300 microns, center to center, the width of the largest grid is approximately 3900 microns, or 3.9 millimeters (less than 1/6 of an inch). The size of the grid, coupled with the limitations on the complexity of the indicia, limits visual inspection of the pattern. Even if the grid were expanded to encompass the entire wafer, the requirement that defects be evenly spaced throughout a grid limits the clarity of the pattern and the contrast between the areas in which the defects are present and the areas in which the defects are omitted.

SUMMARY OF THE INVENTION

The present invention overcomes the aforementioned limitations while enabling the operator to determine the size of the artificial defects on the calibration wafer by visual inspection without reference to any source external to the wafer.

The present invention involves the random distribution of artificial defects onto specific areas of a wafer. These defects are disposed onto the area in sufficient density to form indicia that are visually discernable to the operator when displayed by a detection apparatus. The high density of defects clearly distinguishes the areas in which the artificial defects are present from the areas in which the artificial defects are absent. The dense disposition of the defects further allows for details in the indicia not available when defects are spaced evenly apart. Indicia can indicate numbers with curved edges as well as multiple digits. The indicia are not limited to the size of a predetermined grid. The resulting indicia are, therefore, more readily discernable to the operator when displayed by a detection apparatus. Further, because the indicia can indicate numbers containing multiple digits, the indicia can directly indicate the predetermined size of the artificial defects, allowing the operator to more quickly calibrate the defect inspection system. Finally, multiple indicia can be disposed on a wafer. Each indicium could represent artificial defects of a different size. This allows the operator to calibrate the defect inspection system for a multiplicity of defect sizes using the same wafer.

The present invention further involves a method of distributing artificial defects onto specific areas of a wafer. Artificial defects are introduced into the top of a chamber. A wafer is set on the bottom of the chamber on top of an electrically charged plate. A mask with a predetermined open pattern is positioned above the wafer allowing defects to pass through the open area onto the wafer to form the predetermined indicia.

BRIEF DESCRIPTION OF THE DRAWINGS

Some of the features and advantages of the present invention having been stated, others will become apparent as the description proceeds when taken in conjunction with the accompanying drawings, in which.

DETAILED DESCRIPTION OF ILLUSTRATIVE EMBODIMENTS

The present invention now will be described more fully hereinafter with reference to the accompanying drawings in which preferred embodiments of the invention are shown. This invention may, however, be embodied in many different forms and should not be construed as limited to the illustrated embodiments set forth herein; rather, these embodiments are provided so that this disclosure will be thorough and complete and will fully convey the scope of the invention to those skilled in the art. Like numbers refer to like elements throughout.

Figure 1:
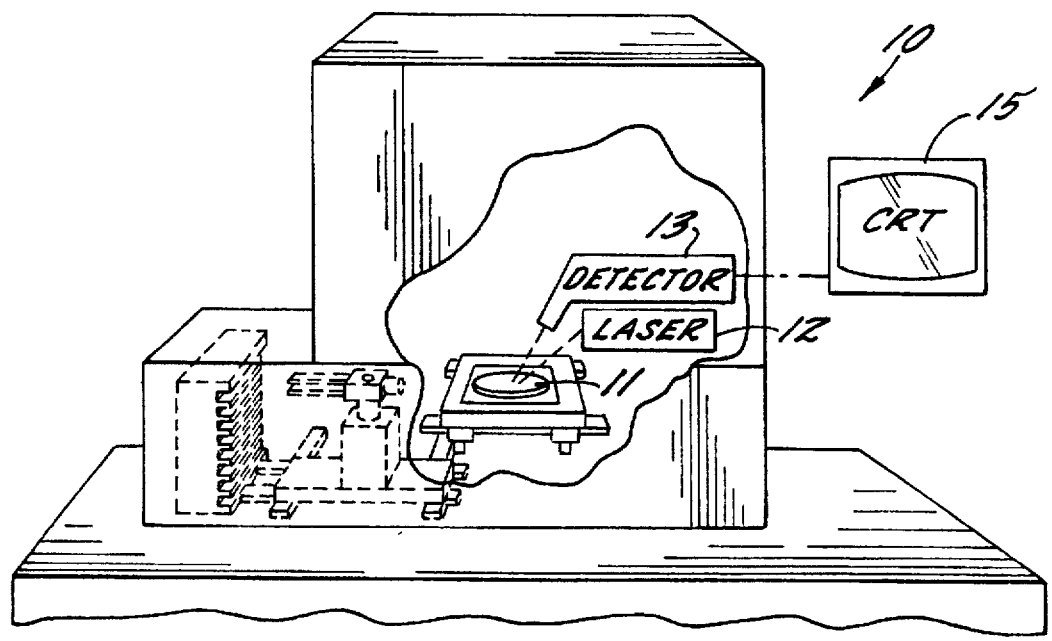
FIG. 1 is a perspective view of a defect inspection system according to the present invention with parts broken away for clarity of illustration.

Referring now to the drawings, FIG. 1 is a perspective view of a defect inspection system, broadly designated at 10 according to the present invention with parts broken away for clarity. A surface to be inspected, such as a semiconductor wafer 11, is positioned such that a beam from a laser 12 is scanned along a predetermined path across the surface of the wafer 11. Light from the laser beam that contacts defects present on the wafer 11 will reflect off the defects and scatter. Light from the laser beam 12 that does not contact the defects on the wafer 11 will be specularly reflected from the wafer 11. A signal detector 13 is used to detect the scattered light from the laser beam 12 and to thereby identify the size and location of the defects. The signal detector 13 converts the scattered light to a voltage signal where a large scattering of light from large defects correspond to a high voltage signal, and where a smaller scattering of light from a smaller defect corresponds to a smaller voltage signal. The voltage signals are converted by computer software to images that can be displayed on a CRT display 15, printer, or any other type of output apparatus.

These defect inspection systems 10 require repeated calibration to ensure their accuracy. Therefore operators will use calibration standards to ensure accurate readings from the defect inspection system.

Figure 2A:
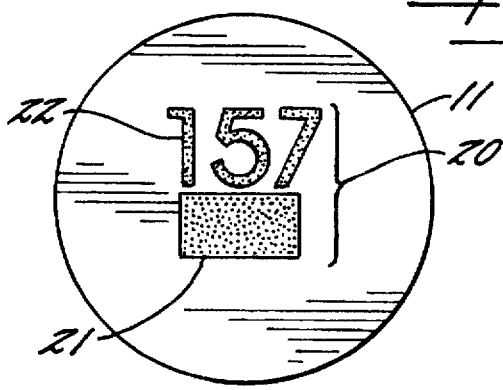
FIG. 2A is a plan view of a substrate in which the artificial defects have been disposed within a predetermined visually discernable indicia.

FIG. 2A is a plan view of the calibration standard in accordance with one embodiment of the invention where the artificial defects have been uniformly disposed on a wafer 11 within a predetermined area to form indicia 20. In the embodiment illustrated, the indicia 20 are comprised of an area where the artificial defects are disposed to form a solid area 21, such as a square or rectangle, and to form a predetermined pattern 22 in close proximity to the solid area 21. The solid area 21 provides an area of sufficient height and width to allow a calibration system to quickly locate an area on the wafer where the artificial defects have been disposed. Because this area 21 is of a greater width than the line forming the pattern 22 of the indicia, a slight misalignment in the defect inspection system is less likely to cause the beam from the laser 12 to sample outside the solid area 21 than to sample outside the width of the pattern 22.

In the embodiment shown, the pattern 22 is in the form of numbers of sufficient size that they can be distinguished when viewed on the CRT display 15. Preferably, the numbers are selected to correspond to the selected size of the artificial defects which form the solid area 21 and the pattern 22. Thus, for example, the number "157" shown in FIG. 2A corresponds to a particle size of 0.157 microns. Although the pattern 22 has been shown in the form of numbers, it will be understood that it can also take the form of letters or any other recognizable form which represents the size of the artificial defects disposed on the pattern 22 and on the solid area 21. The predetermined indicia 20 is readily discernable when viewed through the CRT display (see FIG. 1, 15) or any other output device.

Each artificial defect that makes up the predetermined indicia 20 is randomly disposed with respect to every other artificial defect within the solid area 21 and the pattern 22. When viewing the entire solid area 21 and the pattern 22, however, the distribution of the artificial defects over the entire area is of a generally uniform density and thickness. The artificial defects can be any material that can be produced to form particles of a consistent, known size. The preferred material based on current technology is a polystyrene latex sphere. These spheres can be purchased from Duke Scientific in Palo Alto, Calif., and Japanese Silicon Rubber in Japan. Latex spheres are currently favored because they can form very small, uniform sized particles. Other materials that may be used include aluminum, titanium, tungsten, and nitrites, available from MSP in Minneapolis, Minn. The metals generally scatter more light than a similar sized latex particle, and organics generally scatter less light than a similar sized latex particle. The nature of polystyrene latex spheres does not allow these spheres to scatter light in a manner comparable to real world defects.

The predetermined indicia 20 may be more readily discernable by using colored particles for the artificial defects. These particles may be manufactured in colors that contrast with the color of the wafer 11. Different size particles could be manufactured in different contrasting colors. With sufficient contrast, the indicia 20 may be discernable to the operator without the use of any detection apparatus, resulting in a further reduction of calibration time and complexity. Even if the specific pattern of the indicia cannot be discerned, the operator may be able to discern a colored haze on the wafer surface. Because different colors could be used to represent different sized particles, the operator could view the colored haze and know the size of the artificial defects disposed on that particular wafer.

Figure 2B:
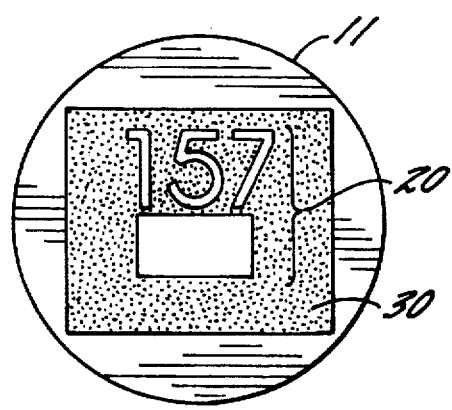
FIG. 2B is a plan view of a substrate in which the artificial defects have been disposed in the area surrounding the predetermined indicia, the area devoid of the artificial defects forming the predetermined visually discernable indicia.

FIG. 2B is a plan view of a calibration standard in accordance with a further embodiment of the invention in which the artificial defects have been uniformly disposed on substrate 11 in the area 30 surrounding the predetermined indicia 20. In this embodiment, the area devoid of the artificial defects forms the predetermined visually discernable indicia 20. The predetermined visually discernable indicia 20 are still present on the wafer 11, so the operator viewing the wafer 11 on the CRT display 15 or other output device can read the indicia 20 to determine the calibration size of the artificial defects.

Figure 2C:
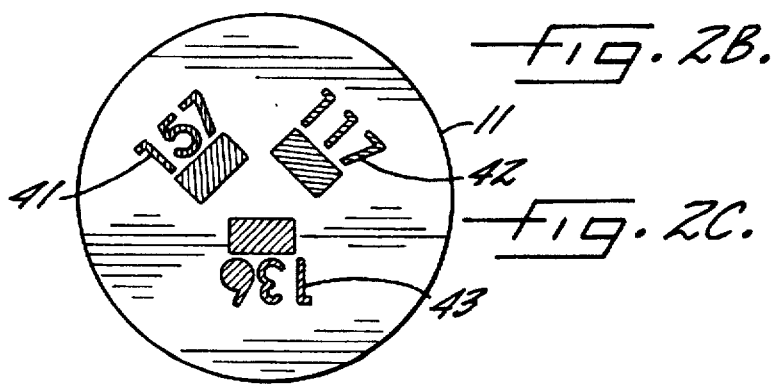
FIG. 2C is a plan view of a substrate in which artificial defects of varying sizes are disposed on different areas of the same substrate, each predetermined visually discernable indicia comprised of uniformly sized artificial defects.

FIG. 2C is a plan view of a calibration standard in accordance with a still further embodiment of the invention in which artificial defects of varying sizes are uniformly disposed on different areas 41, 42, and 43 of the substrate 11. The predetermined visually discernable indicia 20 within each area 41, 42, 43 of the substrate 11, however, includes uniformly sized artificial defects. This embodiment is a modification of FIG. 1 in that more than one artificial defect size is disposed on a single wafer 11. By disposing more than one artificial defect size on a single wafer, operators do not need to use as many wafers, storage for calibration wafers can be reduced, and multiple calibrations of defect inspection systems can be completed without changing wafers. A six-inch wafer may contain three to five separate indicia representing three to five different sizes of artificial defects. A twelve-inch (300 mm) wafer may contain correspondingly more separate indicia representing correspondingly more different sizes of artificial defects.

A further embodiment of the invention (not shown) in which artificial defects of varying sizes are uniformly disposed on different areas of the substrate, as in FIG. 2C, would be a modification of FIG. 2B in which a multiplicity of predetermined visually discernable indicia are formed by voids within areas of artificial defects. These areas within which the defects are disposed would be separated from each other by an absence of artificial defects between each area.

Figure 3A:
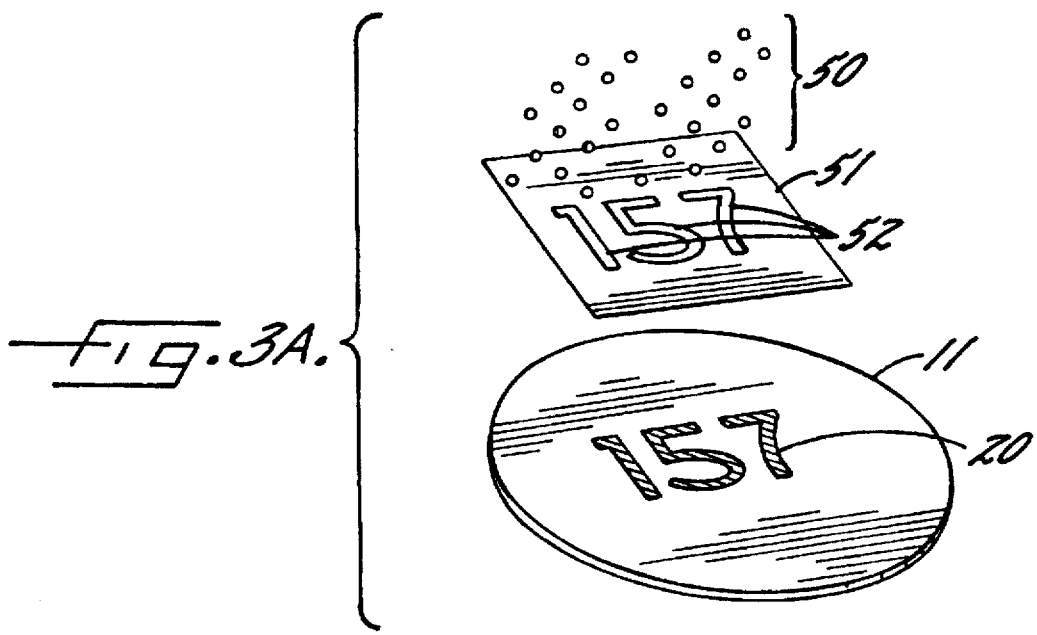
FIG. 3A is a perspective view demonstrating a method of deposition of the artificial defects through a mask and onto the substrate to form a predetermined visually discernable indicia.

FIG. 3A is a perspective view demonstrating a method of deposition of the artificial defects 50 through a mask 51 with a predetermined open pattern and onto the substrate 11 to form a predetermined visually discernable indicia 20. The mask 51 is placed over the wafer 11 such that the predetermined open pattern 52 in the mask 51 overlie the area of the wafer 11 on which the artificial defects 50 will be disposed. Generally, the mask 51 is positioned approximately ⅛ of an inch above the wafer 11. The mask 51 does not touch the wafer 11, but is positioned directly above the wafer 11. The wafer 11 sits on an electrically charged plate (not shown). The mask 51, wafer 11, and plate are positioned inside and at the bottom of a chamber. The interior volume of the chamber is permeated with artificial defects. The weak electrical charge of the plate pulls the defects towards the surface of the wafer 11. The artificial defects 50 are uniformly deposited over the area of the wafer 11. Because of their small size, the artificial defects 50 adhere to the surface of the wafer 11 without the need for adhesives. The mask 51 prevents the deposition of the artificial defects 50 on all areas of the wafer 11 except where the artificial defects 50 pass through the predetermined open pattern 52 of the mask 51. The predetermined open pattern 52 of the mask 51 define the shape of the indicia 20 formed on the wafer 11 by the presence of the artificial defects 50, similar to the indicia shown in FIG. 2A. The indicia shown in FIG. 2C can be formed by repeating this method, depositing different sized artificial defects 50 over different areas 41, 42, and 43 of the wafer 11.

Figure 3B:
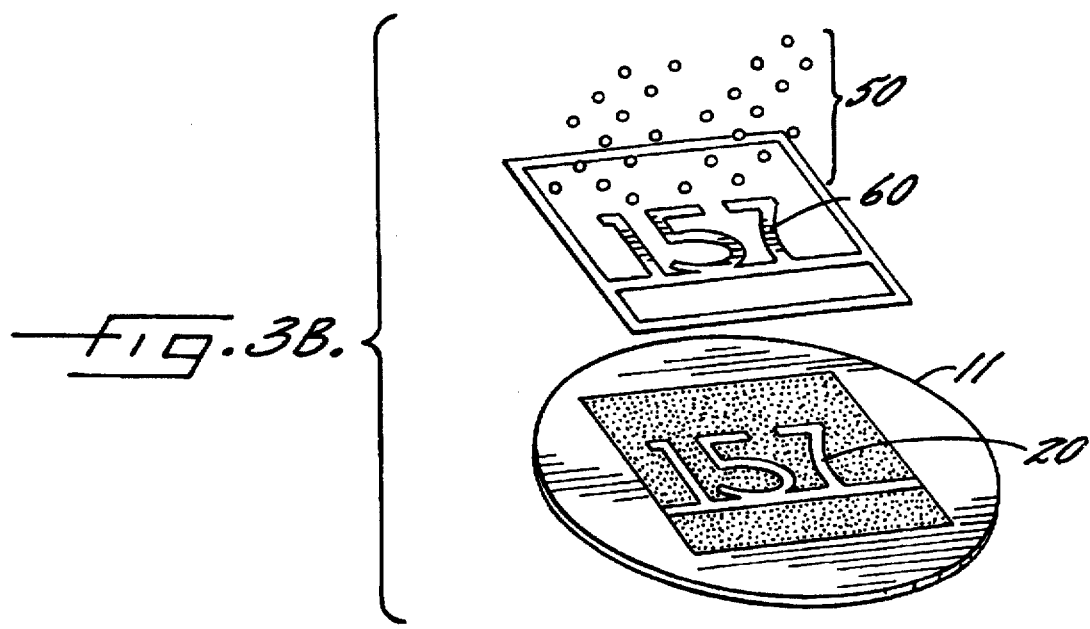
FIG. 3B is a perspective view of a method of depositing artificial defects on the substrate where the defects pass through the mask and onto the substrate, and where the area devoid of artificial defects forms the predetermined visually discernable indicia.

FIG. 3B is a perspective view of a method of depositing artificial defects 50 on the substrate 11 where the defects 50 again pass through the mask 51 and onto the substrate, similar to FIG. 3A. In FIG. 3B, however, the closed area 60 of the mask 51 forms the predetermined visually discernable indicia 20 on the wafer 11. Therefore, the visually discernable indicia 20 are represented by the areas devoid of artificial defects, similar to the indicia shown in FIG. 2B.

Prior to entry into the chamber where the artificial defects are deposited on the wafer 11, the artificial defects are prepared for deposition. As previously noted, polystyrene latex spheres are the preferred form of artificial defects currently in use. These artificial defects can be purchased from the suppliers previously mentioned in the form of a heavily concentrated solution or in a premixed solution with deionized water. If the defects are purchased in a heavily concentrated form, the solution is diluted by placing two or three drops of the concentrated solution in approximately 100 milliliters of deionized water. Next, the spheres are placed in an aspirator where the defects are separated from the solution. The spheres are then processed through a classifier which separates the defects from each other and prevents clumping. Finally, the spheres are placed in a dryer where the remaining solution is evaporated. From this point, the particles are placed inside the chamber where they are disposed on the wafer 11 in the manner previously described.

Figure 4:
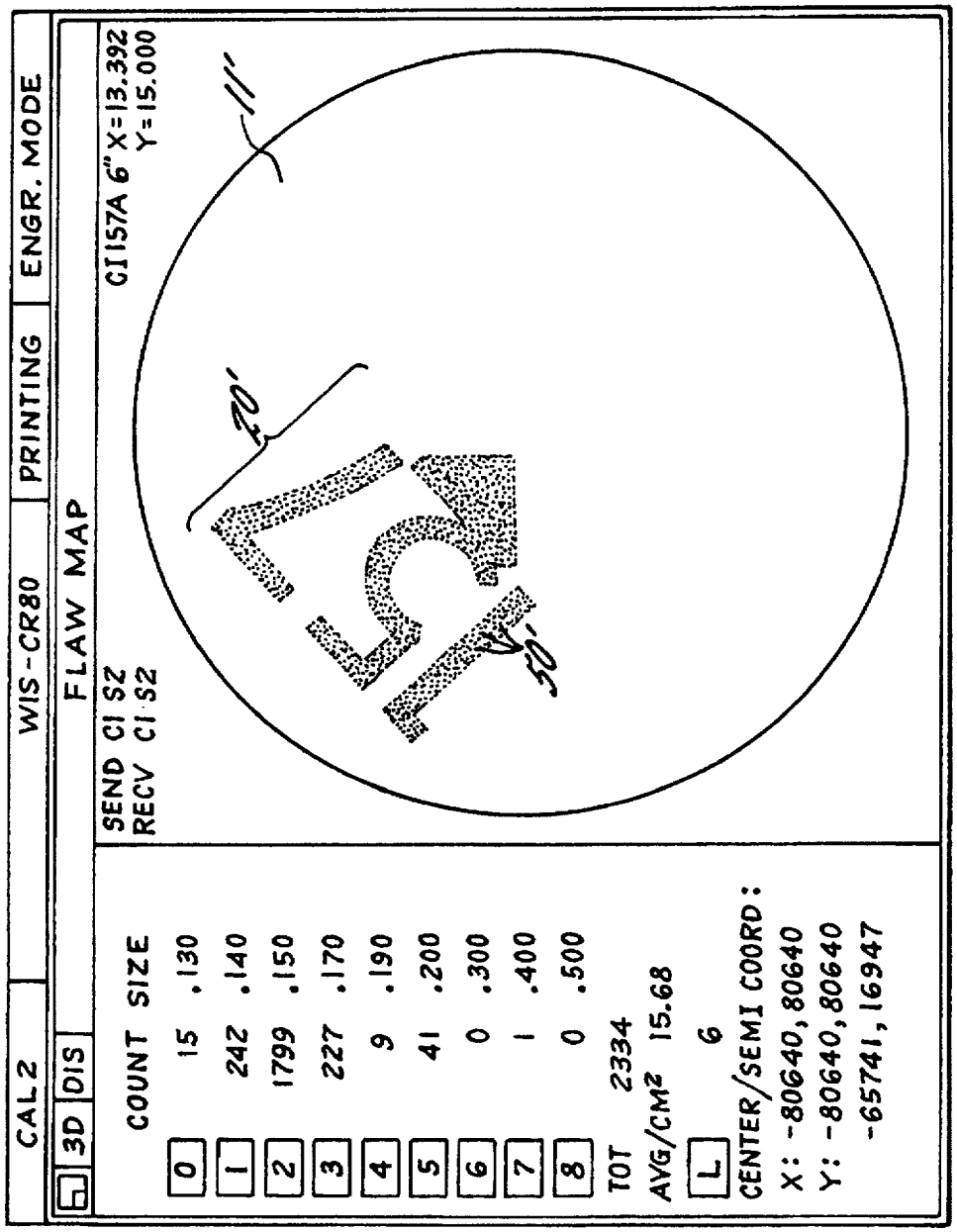
FIG. 4 is a representation of the actual visual display as viewed by an operator of the defect inspection system.

FIG. 4 is a representation of the actual visual display 70 as viewed by the operator through a CRT display 15. A similar display can be produced by a printer or other output device. The CRT display 15 or other output device can show images of the artificial defects 50' and the predetermined indicia 20' as they appear on the wafer 11'. The display 70 can provide additional information regarding the actual size of each artificial defect detected. Most of the artificial defects recognized in FIG. 4 are approximately 0.140 to 0.170 microns in diameter. This is consistent with the image of the indicia 20' which displays "157." This indicia 20' tells the operator that the artificial defects 50 disposed on this wafer are 0.157 microns in diameter. These measurements confirm the expected size of the artificial defects, thereby confirming that the defect inspection system is calibrated. This range in the diameter of the artificial defects is for illustration purposes only and does not indicate a limit as to the size of the artificial defects that may be used. For example, defect inspection systems are currently being developed that will be able to recognize artificial defects of 0.060 microns in diameter or smaller.

In the drawings and specification, there has been disclosed a typical preferred embodiment of the invention and, although specific terms are employed, they are used in a generic and descriptive sense only and not for the purposes of limitation, the scope of the invention being set forth in the following claims.

That which is claimed:

1. A calibration standard for calibrating a defect inspection system, the calibration standard comprising:

a substrate; and a multiplicity of artificial defects of a predetermined uniform size disposed on a selected area of said substrate, said defects being randomly spaced with respect to one another within said selected area and of sufficient density to form a visually discernable contrast with adjacent portions of the substrate surface which are devoid of said defects, said visually discernable contrast with adjacent portions of the substrate forming predetermined visually discernable indicia.

2. A calibration standard according to claim 1, wherein said visually discernable indicia corresponds to a character representing the predetermined size of the defects to allow a user to readily identify the selected defect size by viewing the calibration standard.

3. A calibration standard according to claim 1, wherein said multiplicity of defects are of a first predetermined uniform size and disposed on a first selected area of said substrate, and said standard additionally includes a further multiplicity of artificial defects of a second predetermined uniform size different from said first size disposed on a second selected area of said substrate, said defects being randomly spaced within said second selected area and of sufficient density to form a visually discernable contrast with adjacent portions of the substrate which are devoid of said defects.

4. A calibration standard according to claim 3, wherein said visually discernable contrast within said second area forms predetermined visually discernable indicia corresponding to a character representing said second predetermined size of artificial defects.

5. A calibration standard according to claim 1, wherein said calibration standard is a wafer of a semiconductor material.

6. A calibration standard according to claim 1, wherein said artificial defects are polystyrene latex spheres.

7. A calibration standard according to claim 1, wherein said artificial defects are disposed at a uniform density within said selected area of said substrate.

8. A calibration standard according to claim 7, wherein said visually discernable indicia correspond to characters representing the predetermined size of the defects to allow a user to readily identify the selected defect size by viewing the calibration standard.

9. A calibration standard according to claim 1, wherein said portions of the substrate surface which are devoid of said artificial defects form said predetermined visually discernable indicia.

10. A calibration standard according to claim 9, wherein said visually discernable indicia corresponds to characters representing the predetermined size of the defects to allow a user to readily identify the selected defect size by viewing the calibration standard.

11. A calibration standard for calibrating a defect inspection system, the calibration standard comprising:
    a wafer of a semiconductor material; and
    a multiplicity of polystyrene latex spheres of predetermined uniform size disposed on a selected area of said wafer, said spheres being randomly spaced with respect to one another within said selected area and of sufficient density to form a visually discernable contrast with adjacent portions of the wafer which are devoid of such spheres, said spheres defining predetermined visually discernable indicia corresponding to a numerical character representing the predetermined size of the spheres.

12. A calibration standard according to claim 11, wherein said multiplicity of defects are of a first uniform predetermined size and disposed on a first selected area of said substrate, and said standard additionally includes a further multiplicity of artificial defects of a second uniform predetermined size different from said first size disposed on a second selected area of said substrate, said defects being randomly spaced within said second selected area and of sufficient density to form a visually discernable contrast with adjacent portions of the substrate which are devoid of said defects.

13. A calibration standard for calibrating a defect inspection system, the calibration standard comprising:
    a wafer of a semiconductor material; and
    a multiplicity of polystyrene latex spheres of predetermined uniform size disposed on a selected area of said wafer, said spheres being randomly spaced with respect to one another within said selected area and of sufficient density to form a visually discernable contrast with adjacent portions of the wafer which are devoid of such spheres, and said adjacent portions of the wafer surface which are devoid of such spheres defining predetermined visually discernable indicia corresponding to a numerical character representing the predetermined size of the spheres.

14. A method of forming a calibration standard for a defect inspection system, the method comprising:
    (a) positioning a mask having a predetermined open pattern formed therein in overlying relation to a substrate, the predetermined open pattern being of a size less than the overall area of the substrate; and
    (b) passing defects of a predetermined uniform size through the predetermined open pattern of the mask and onto the surface of the substrate to thereby form predetermined visually discernable indicia corresponding to the predetermined open pattern of the mask.

15. The method according to claim 14, wherein said step of positioning a mask includes positioning a mask having an open pattern corresponding to the predetermined visually discernable indicia to be formed on the surface of the substrate.

16. The method according to claim 15, wherein the open pattern of the mask is configured to define one or more numerical characters, and further comprising the step of selecting defects of a predetermined uniform size which correspond to the numerical characters defined by the predetermined open pattern of the mask.

17. The method according to claim 14, wherein said step of positioning a mask includes positioning a mask having an open pattern corresponding to areas adjacent to the predetermined visually discernable indicia so that the areas devoid of defects form the predetermined visually discernable indicia.

18. The method according to claim 17, wherein the open pattern of the mask is configured to define the outline of one or more numerical characters, and further comprising the step of selecting defects of a predetermined uniform size which correspond to the numerical characters indicated by the predetermined open pattern of the mask.

19. A method of calibrating a defect inspection system comprising:
    positioning in a particle detection system a calibration standard which includes a multiplicity of artificial defects of a predetermined uniform size disposed on a selected area of a substrate, the defects being randomly spaced with respect to one another and of sufficient density to form visually discernable indicia in the form of one or more characters representing the size of the artificial defects;
    measuring the size of the artificial defects using the particle detection system;

identifying the size of the artificial defects on the calibration standard by viewing the one or more characters on the surface of the calibration standard; and comparing the size of the artificial defects as determined by the particle detection system with the thus identified size represented by the characters formed on the calibration standard to determine the accuracy of the particle detection system.

20. The method according to claim 19, wherein the multiplicity of defects are of a first predetermined uniform size and disposed on a first selected area of the substrate, and the standard additionally includes a further multiplicity of artificial defects of a second predetermined uniform size different from the first size disposed on a second selected area of the substrate, the defects being randomly spaced within the second selected area and of sufficient density to form visually discernable indicia in the form of one or more characters representing said second uniform size;

selecting one of said first and second areas of the substrate and measuring the size of the artificial defects in the selected area using the particle detection system; and identifying the size of the artificial defects in the selected area of the substrate by viewing the one or more characters formed within said area of the substrate.

* * * * *